United States Patent
Nissim et al.

[11] Patent Number: 5,760,694
[45] Date of Patent: Jun. 2, 1998

[54] MOISTURE DETECTING DEVICES SUCH AS FOR DIAPERS AND DIAPERS HAVING SUCH DEVICES

[75] Inventors: Ofer Nissim, Pound Ridge, N.Y.; Donald B. Ellingham, Fairfield, Conn.; David Janszen, New York, N.Y.

[73] Assignee: Knox Security Engineering Corporation, Norwalk, Conn.

[21] Appl. No.: 646,453

[22] Filed: May 7, 1996

[51] Int. Cl.$^6$ .................................................. G08B 21/00
[52] U.S. Cl. .......................... 340/604; 340/603; 128/885; 128/886
[58] Field of Search ........................ 340/573, 602, 340/603, 604, 605; 128/885, 886; 604/361

[56] References Cited

U.S. PATENT DOCUMENTS

| | | | |
|---|---|---|---|
| 3,759,246 | 9/1973 | Flack et al. | 128/886 |
| 4,069,817 | 1/1978 | Fenole et al. | 128/886 |
| 4,099,118 | 7/1978 | Franklin et al. | 324/61 R |
| 4,106,001 | 8/1978 | Mahoney | 340/604 |
| 4,163,449 | 8/1979 | Regal | 340/573 |
| 4,191,950 | 3/1980 | Levin et al. | 340/604 |
| 4,205,672 | 6/1980 | Dvorak | 128/886 |
| 4,264,901 | 4/1981 | Petersen | 340/604 |
| 4,356,818 | 11/1982 | Macias | 128/886 |
| 4,484,573 | 11/1984 | Yoo | 128/886 |
| 4,539,559 | 9/1985 | Kelly | 215/42 |
| 4,640,276 | 2/1987 | Jin-Sheng | 128/886 |
| 4,653,491 | 3/1987 | Okada | 128/886 |
| 4,657,039 | 4/1987 | Bireley | 137/78.3 |
| 4,688,027 | 8/1987 | Widener | 340/604 |
| 4,692,752 | 9/1987 | Abel | 340/604 |
| 4,704,108 | 11/1987 | Okada | 604/361 |
| 4,738,260 | 4/1988 | Brown | 128/138 A |
| 4,754,264 | 6/1988 | Okada | 340/573 |
| 4,760,383 | 7/1988 | DiLorenzo | 340/573 |
| 4,768,023 | 8/1988 | Xie | 340/573 |
| 4,796,014 | 1/1989 | Chia | 340/573 |
| 4,800,370 | 1/1989 | Vetecnik | 340/573 |
| 4,977,906 | 12/1990 | Di Scipio | 128/885 |
| 5,036,859 | 8/1991 | Blakeney | 128/734 |
| 5,043,704 | 8/1991 | Blakeney | 340/573 |
| 5,047,750 | 9/1991 | Hector | 340/573 |
| 5,121,630 | 6/1992 | Calvin | 73/73 |
| 5,210,500 | 5/1993 | Pingel et al. | 324/667 |
| 5,226,928 | 7/1993 | Johnson | 48/94 |
| 5,264,830 | 11/1993 | Kline et al. | 340/604 |
| 5,291,181 | 3/1994 | DePonte | 340/604 |
| 5,335,664 | 8/1994 | Nagashima | 340/573 |
| 5,392,032 | 2/1995 | Kline et al. | 340/604 |
| 5,395,358 | 3/1995 | Lu | 604/361 |
| 5,468,236 | 11/1995 | Everhart | 604/361 |
| 5,469,145 | 11/1995 | Johnson | 340/604 |
| 5,469,146 | 11/1995 | Gurler | 340/605 |
| 5,486,815 | 1/1996 | Wagner | 340/602 |
| 5,537,095 | 7/1996 | Dick | 340/605 |
| 5,557,263 | 9/1996 | Fisher et al. | 340/605 |
| 5,568,128 | 10/1996 | Nair | 340/604 |
| 5,570,082 | 10/1996 | Mahgerefteh et al. | 340/604 |

FOREIGN PATENT DOCUMENTS

| | | |
|---|---|---|
| 0 446 821 A2 | 9/1991 | European Pat. Off. |
| WO 94/07224 | 3/1994 | WIPO |
| WO 94/22401 | 10/1994 | WIPO |

*Primary Examiner*—Thomas Mullen
*Assistant Examiner*—Ashok Mannava
*Attorney, Agent, or Firm*—Stanger & Dreyfus, P.C.

[57] ABSTRACT

A pair of spaced electrodes within an area subject to wetness couple non-conductively with a sensor protected from wetness, and an alarm sounds in response to moisture decreasing the resistance between the electrodes. For example the electrodes project into the absorbent material of a diaper and extend along the inside of the diaper sheath opposite a pouch on the outside of the sheath. The pouch contains a sensor capacitively coupled to the electrodes.

43 Claims, 7 Drawing Sheets

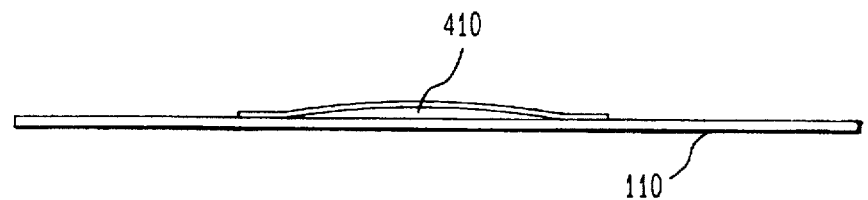
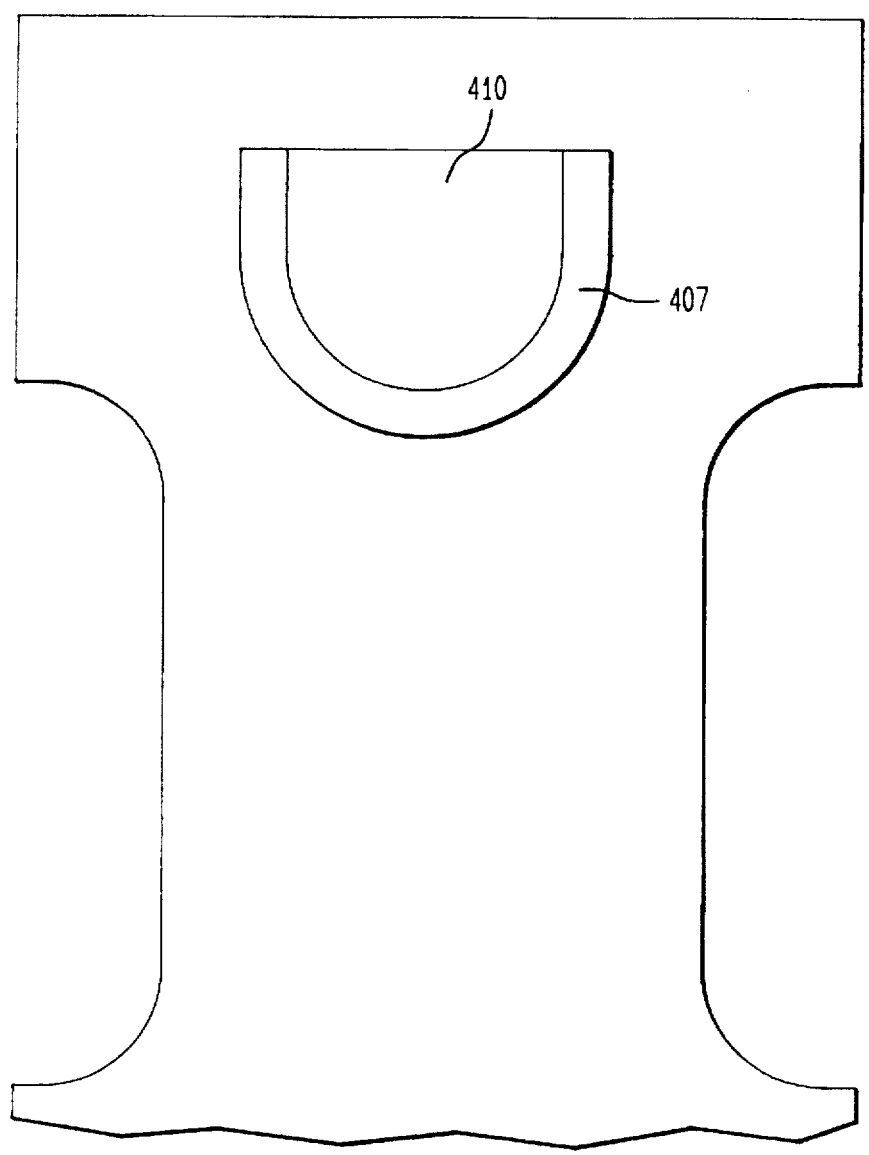

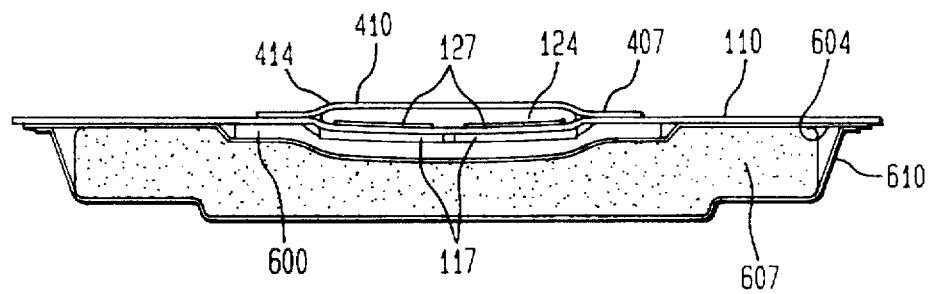
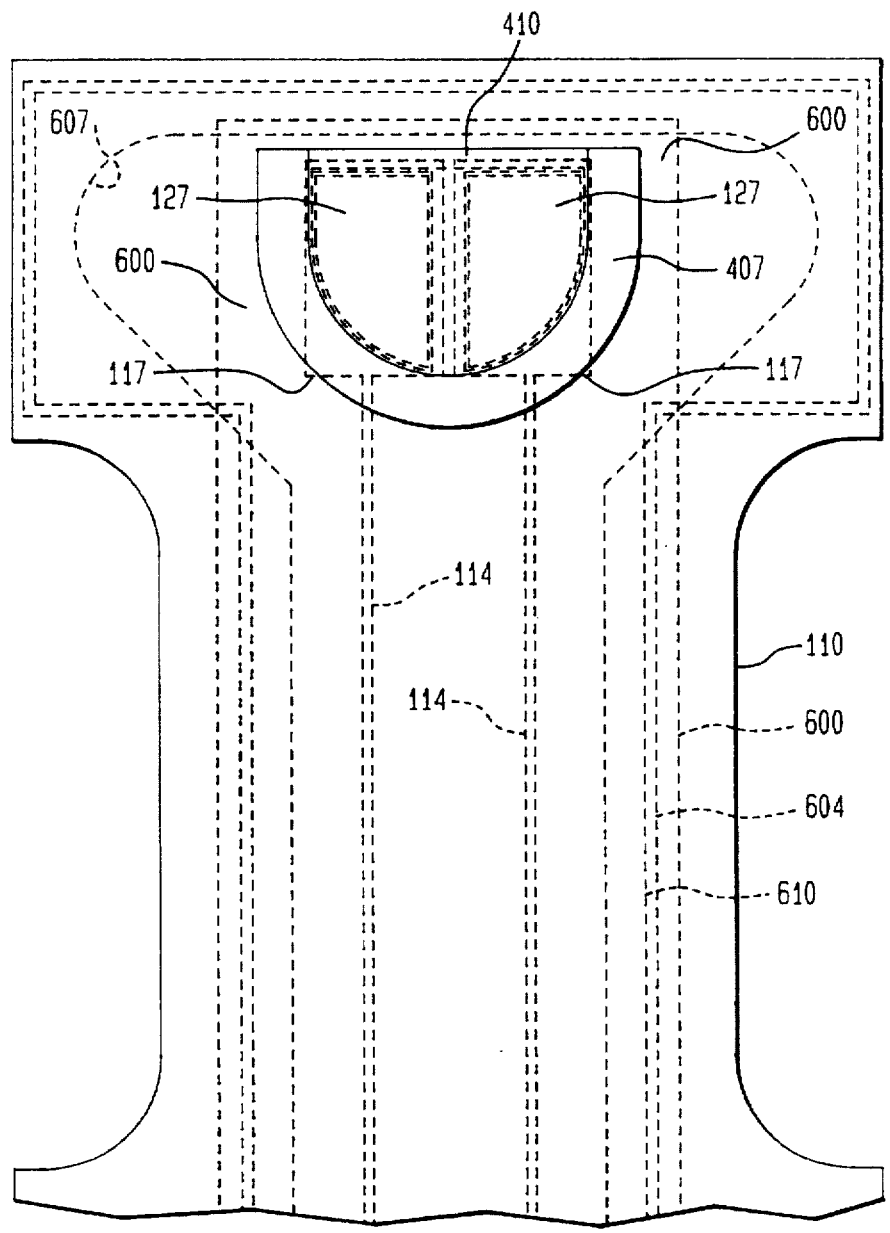

MOISTURE DETECTING DEVICES SUCH AS FOR DIAPERS AND DIAPERS HAVING SUCH DEVICES

FIELD OF THE INVENTION

This invention relates to devices for monitoring wetness, particularly in diapers, and to diapers containing such devices.

BACKGROUND OF THE INVENTION

Various methods and means have been developed for monitoring moisture or wetness in diapers. The purpose of such devices is to set off an alarm when a diaper becomes wet. This permits a mother to tend to a newborn infant or toddler. However such devices have disadvantages in that they may require conductors to pass mechanically through the diaper's plastic outer sheath, may subject the skin of the wearer to direct voltages from a voltage source, may be sensitive only in a limited area, may accidentally respond to the wearer sitting on a wet or metal bench or park slide, or have other drawbacks.

SUMMARY OF THE INVENTION

According to an embodiment of the invention, a pair of spaced electrodes within the area subject to wetness couple non-conductively with a sensor protected from wetness, and an alarm sounds in response to moisture decreasing the resistance between the electrodes. For example the electrodes project into the absorbent material of a diaper and extend along the inside of the diaper sheath opposite a pouch on the outside of the sheath. The pouch contains a sensor capacitively coupled to the electrodes.

The various features of novelty which characterize the invention are pointed out in the claims forming a part of this specification. Objects and advantages of the invention will become evident from the following detailed descriptions of embodiments of the invention when read in light of the following drawings.

BRIEF DESCRIPTION OF THE DRAWINGS

FIGS. 4 and 5 illustrate an embodiment of a pouch in FIGS. 1 and 2.

FIG. 6 is a plan view of the rear of an embodiment of a diaper with a pouch on the outside and containing a sensor.

FIG. 7 is an frontal elevation of the rear of the diaper, when opened, in FIG. 6.

DETAILED DESCRIPTION OF PREFERRED EMBODIMENTS

Figure 1:
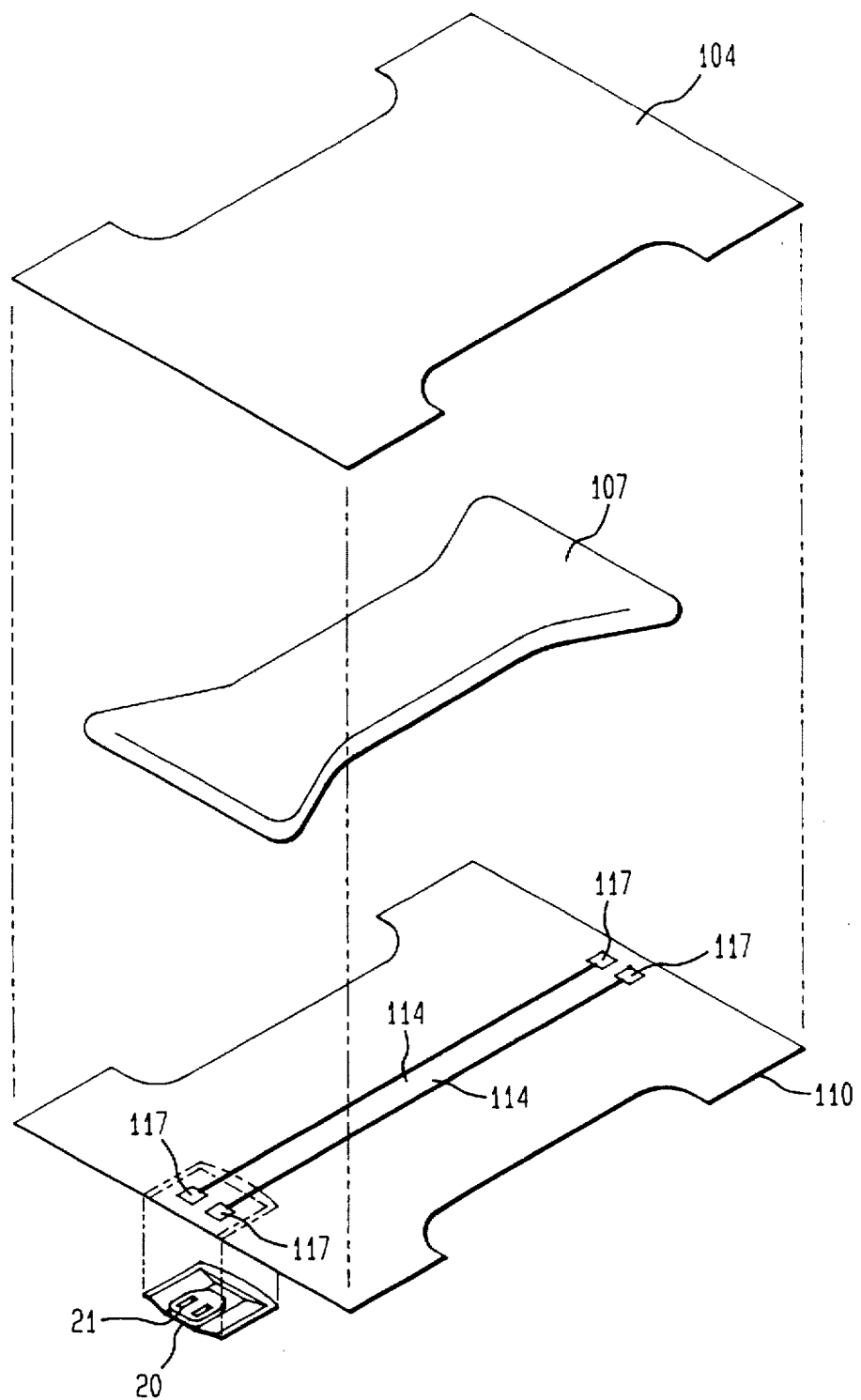
FIG. 1 is an exploded view of a diaper embodying the invention.
Figure 2:
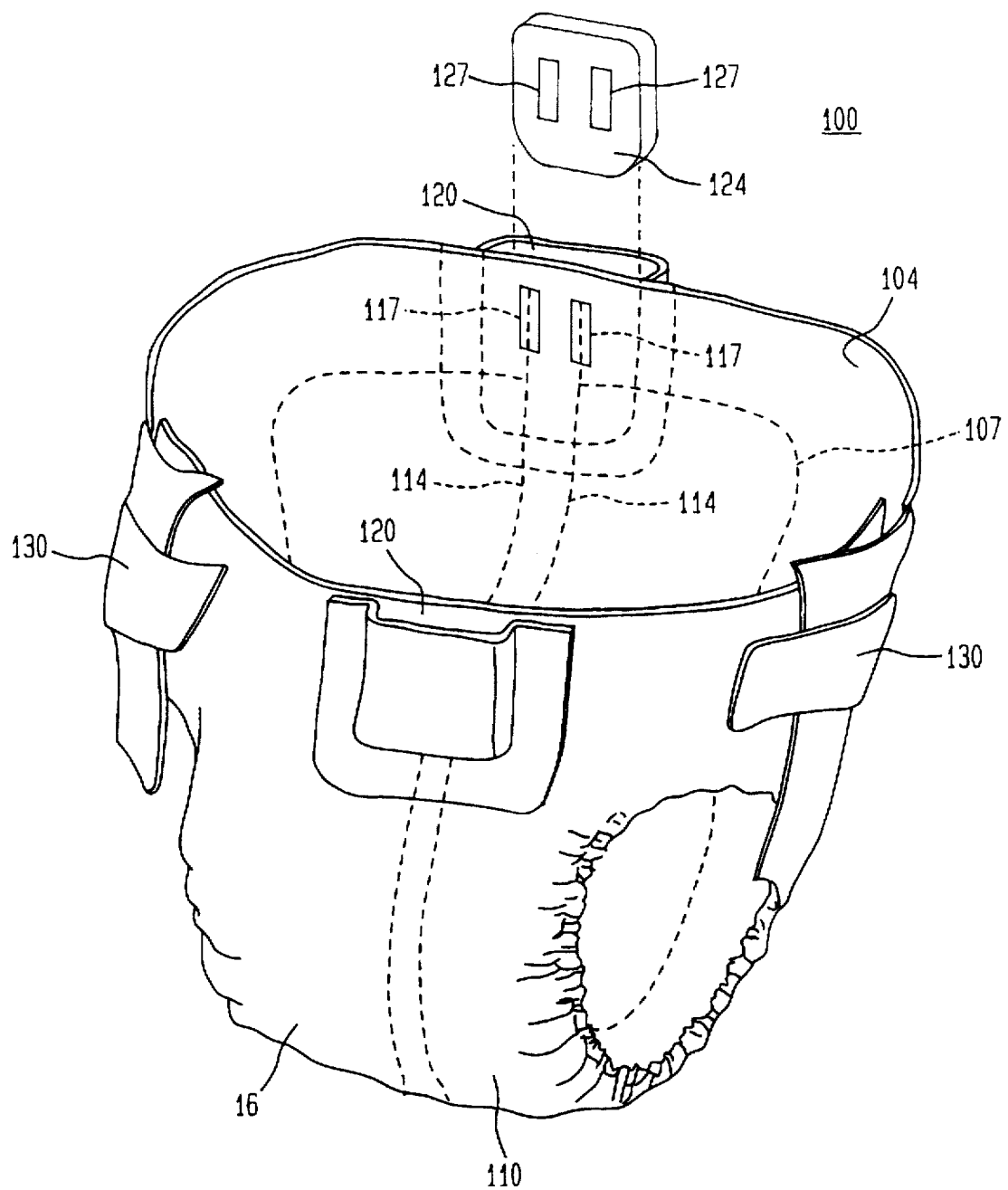
FIG. 2 is a perspective view of FIG. 1.

In the exploded view of FIG. 1 and the partially-exploded perspective of FIG. 2, a disposable diaper 100 embodying the invention includes an inner sheet 104 of a water-permeable film which overlies a wetness absorber layer 107 of powerfully liquid-absorbent padding or other powerfully absorbent material. In one embodiment the layer 107 may include a gel-forming absorbent resin. An outer water-impermeable electrically-insulating plastic sheath 110 supports two conductive spaced-apart electrodes 114, in the form of metallic or other electrically-conductive strips, that extend along the center of the sheath 110 and in electrical contact with the absorber layer 107. According to an embodiment of the invention, the electrodes 114 pass longitudinally through the layer 107. According to another embodiment, the electrodes 114 are in the form of conductive threads or wires.

The sheet 104 is common to most disposable diapers and is often referred to as cover stock. It is composed of thick porous, relatively hydrophobic, bonded fibers which tend to pass liquid in one direction from the wearer to the absorber layer 107. The urine is held away from the skin by the competition between the highly absorbent layer 107 and the not-so-absorbent sheet 104. In this way the relatively hydrophobic fibers space the wet mass of the layer 107 from the skin of the wearer. This keeps the skin dry even when the wearer has wet the diaper. The sheet 104 may be omitted in training diapers that intend to make the wearer uncomfortable when the diaper is wet. The diaper is worn in the usual fashion.

The electrodes 114 terminate in widened pairs of adjacent fixedly spaced electrically-conductive pads 117 on each end. The pairs of pads 117 at each end are printed on the sheath 110 or are bonded to the sheath 110 so they maintain a fixed position on the sheath 110 and so they are in intimate contact with the sheath. According to another embodiment, the pads 117 are otherwise deposited or applied, such as by selective metallization, or carbonization using a laser. Bonded to the outer face of the sheath 110, directly opposite the pads 117 at each end of the sheath, are pouches 120. Each pouch 120 is adapted to receive a removable sensor 124 having thin electrically-conductive rectangular planar members or surfaces 127. Although two pouches 120 exist, only one pouch receives a sensor 124. When two pouches exist, the selection of the pouch which receives the sensor 124 depends upon the preferences, e.g. based on the comfort, of the user.

The position of each pouch 120 is such as to place the pair of planar members 127 on the sheath 110, directly behind a pair of the pads 117 without overlapping one member 127 with two of the opposing adjacent pads 117 or vice versa. One of the pairs of pads or members is larger than the other to permit tolerance in placement.

According to an embodiment, each pouch 120 is composed of or contains, in some portion, resilient material (not shown) to press the members 127 into position against the sheath 110 when the diaper is worn. The members 127 do not electrically contact the pads 117, rather the sheath 110 separates the members from the pads. When a sensor 124 sits in the pouch 120, the pair of members 127 of the sensor 124, and the opposing pair of pads 117 form two adjacent capacitors.

According to an embodiment, the sides of the sensor 124 are tapered to facilitate insertion in the collapsed pouch. The faces of the sensor 124 may also be tapered.

As shown in FIG. 2, suitable fastening strips 130 secure the diaper in operable condition, and the sensor 124 is placed in the pouch 120 at the rear or front of the diaper. When a user wears and wets the diaper, the liquid passes through the sheet 104 into the absorber layer 107 and to the sheath 110.

The liquid then electrolytically short-circuits the electrodes 114. Hence the electrodes 114 operate as a conductive switch which is open, i.e. non-conductive, in a dry diaper and closed, i.e. conductive, in a wet diaper.

According to another embodiment of the invention, the diaper contains only one pouch 120. The diaper may further comprise other accessories as may be necessary or desired, such as elastic electrodes for close fit to the wearer, tapes, tabs, snaps or the like for fastening the diaper in place upon the wearer, for example.

The sensor 124 contains an oscillating voltage or pulse source, preferably one having a low duty cycle, which capacitively couples to the members 127 to the pads 117 using the sheath 110 as the dielectric medium, and an alarm device which responds to the source. The spaced electrodes 114 form a switch that remains open (non-conductive) when the diaper is dry. The sensor 124 is set so varying current from the source cannot pass through the open switch formed by the electrodes 114. When the diaper is wet, the electrolytic action of the urine in the diaper contacts the electrodes 114 and closes the switch, i.e. makes it conductive across the gap between the electrodes 114. The sensor 124 is set so varying voltage of the source then passes a current from the sensor 124 through the capacitor formed by one member 127 and the opposing pad 117, through one electrode 114 through the electrolytically conductive gap between electrodes to the other electrode 114, through the capacitor formed by the second of the pair of pads 117 and the second of the pair of members 127, back to the sensor. The resulting current triggers an alarm which, according to one embodiment, energizes a piezoelectric sounder and plays a tune or makes some other sound such as a beep.

According to another embodiment, the alarm takes the form of a blinking or turned on light, such as an LED. According to another embodiment, the alarm is transmitted by radio waves, infra-red radiation, or other means to a remote position where an attendant can monitor a number of children or other wearers.

The alarm, in the form of a sound or light, informs the wearer, who may be an infant being trained, or the infant's parent, that the diaper is becoming wet. This allows prompt action. A sound or light alarm may for example make the infant in training associate its urges with its training needs. The sound or light can also serve to notify an infant's parent that the child's diaper needs changing. A sound or light alarm can inform a toddler's attendant of these needs. A sound alarm can be an aid in enuresis training. A light alarm can also warn an elderly incontinent or handicapped person without sensation in the peritoneal area of an incident, or inform a caregiver of the need for changing.

The sensor 124 sets an alarm threshold sufficiently high to prevent a false alarm when a wearer sits on a metal bench or on a wet surface. The capacitive impedance between the pads 117 and members 127 is far less than that between the electrodes 114, even when the electrodes 114 are in the vicinity of metal or a wet s surface. Thus the electrodes 114 present a high impedance unless shorted electrolytically by urine in the diaper. The sensor threshold is sufficiently high to avoid responding to the capacitive coupling between the dry electrodes 114, and yet low enough to respond to the electrolytic conduction between the electrodes 114.

Figure 3:
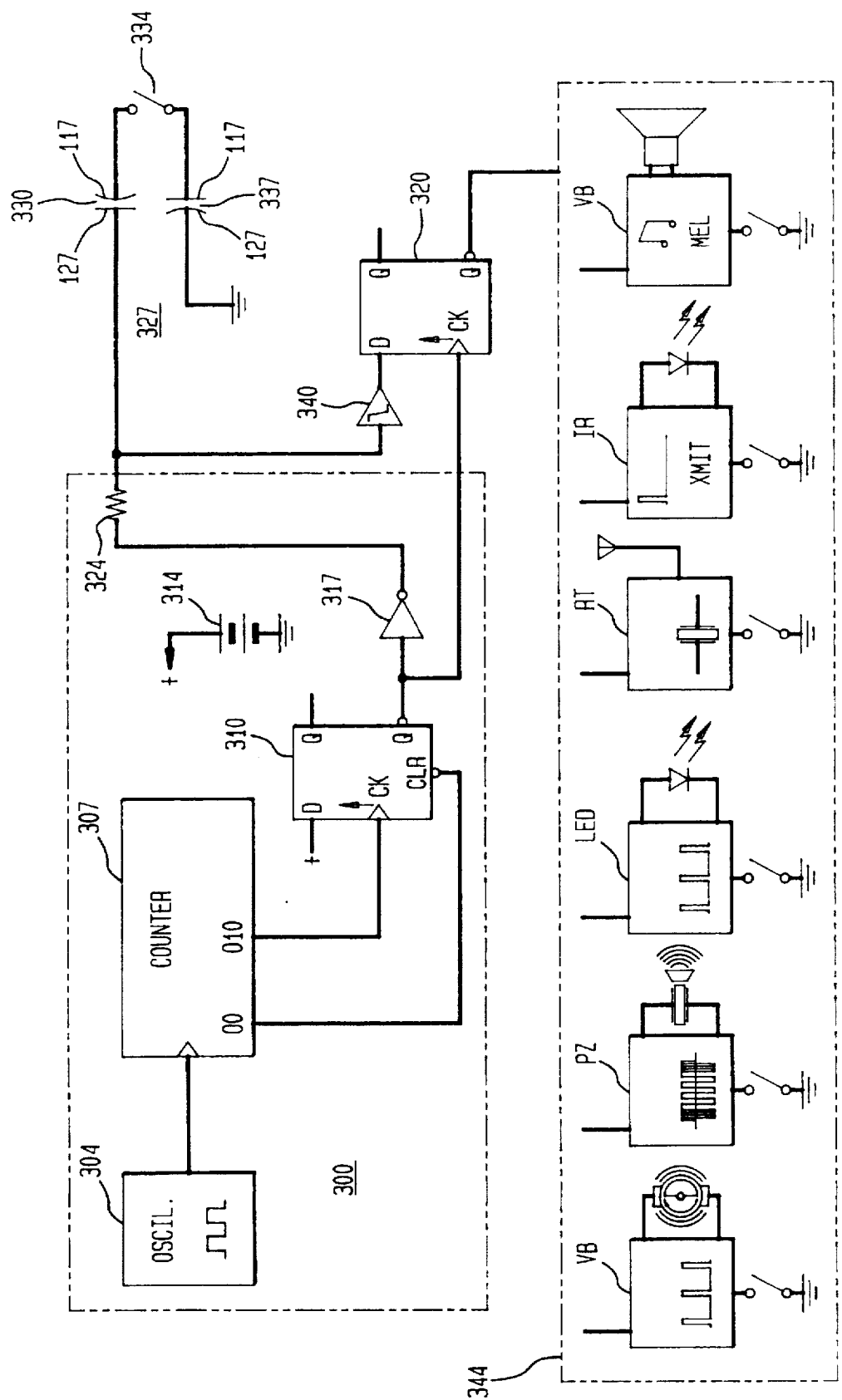
FIG. 3 is circuit diagram of a sensor used in FIGS. 1 and 2.

Details of electrical portions of one embodiment of sensor 124 appear in FIG. 3 which includes a low duty-cycle pulser 300. In the pulser 300, an oscillator 304 and divider counter 307, forming part of an integrated circuit or chip, provide the time base for all events in the wetness detection process. In one embodiment, the counter 307 yields a low frequency pulse rate such as 30 Hz to a rising-edge sensitive clock input of a D-type flip-flop 310. A higher frequency pulse, some derivative of the same clock, e.g. 60 kHz to result in a 1:2000 duty cycle, furnishes a reset to the flip-flop 310 a brief period later. As a consequence, the flip-flop 310, which has its data input connected to a positive supply 314, clocks in a logic high which is reset 15 microseconds later by the higher frequency clock. The inverting output Q' of the flip-flop 310 is used and a corresponding 15 microsecond logical low pulse is subsequently generated. This low pulse appears at an inverting amplifier 317 which drives an output pin on the chip, and also appears at a rising-edge sensitive clock input of second flip-flop 320. The buffered output pulse from the inverter 317 passes to an external resistor 324.

The external resistor 324 performs a charge current limiting function in the external R/C circuit formed with the diaper's capacitor-switch network 327. The latter includes a first capacitor 330 formed by one of the members 127 and one of the pads 117 facing each other across the sheath 110, the resistance 334 of the switch formed by the electrodes 114 and the gap between them, and a second capacitor 337 formed by the other of the members 127 and the other of the pads 117 facing each other across the sheath 110.

The voltage at the resistor 324 and across the capacitor switch network 327 also appears at a Schmidt input buffer 340 which produces an output at the D input of the flip-flop 320. The flip-flop 320 is set at power-up to avoid a brief alarm. An output Q' of the flip-flop 320 drives an alarm 344. In the example shown in FIG. 3, the alarm 344 includes a beep-producing piezoelectric crystal PZ, an LED, a radio transmitter RT, an infra-red transmitter IR, a music generating circuit MG, and a tactilely-sensible vibrator VB for enuresis training, any of which may be energized selectively, either alone or all together. The piezoelectric crystal PZ may also produce ultrasonic chirps to communicate the alarm to a remote or bedside receiver. According to other embodiments of the invention, the sensor 124 includes any one or more of the crystal, LED, radio transmitter, infra-red transmitter, music generating circuit, or a tactilely-sensible vibrator without the others. The others may be omitted. Other means of alarm may be used.

In each charge cycle a 15 microsecond current-limited pulse feeds into the capacitor-switch network 327. Assuming the network 327 is initially discharged, it begins to acquire a charge, the terminal voltage of which is a function of the charging source voltage, current-limiting resistor 324, the pulse length, and the capacitance of the series-connected capacitors in the sensor network 327. When the diaper is dry the open circuit at the switch 324 between the electrodes 114 allows the charge across the circuit 327 to rise rapidly toward its peak and beyond the threshold of the Schmidt trigger 340. This places a low at the output Q' of the flip-flop 320. This holds the alarm 320 off. The voltage rises rapidly because, in the proximity of the dry layer 107, the total capacitance of circuit 327 is extremely low, much lower than the series capacitance of the capacitors 330 and 337.

When urine electrolytically shorts the electrodes 114, the total capacitance of network 327 rises substantially to approximately the series combination of the value of the far higher capacitance of coupling capacitances 330 or 337. The voltage across the network 327 then fails to rise above the positive-going threshold of the Schmidt trigger 340. At the next pulse, when the flip-flop 310 resets the flip-flop 320, the output at Q' of the flip-flop 320 goes high and triggers the alarm 344.

More specifically, the resistor 324 has a value such that the network 327 charges to at least the threshold (typically 1.6 volts) of a Schmidt input buffer 340, when the diaper is dry. Thus, at the time of charge termination, and the exact moment when the synchronous rising-edge clock is fed to the second flip-flop 320, the instantaneous level of the output of the Schmidt input buffer 340, being a function of its presently imposed input voltage, is clocked into the sampling flip-flop 320. The resulting state of the outputs of flip-flop 320 indicate the wet or dry state of the diaper in that previous instant and the whole cycle recurs at the previously mentioned 30 Hz rate. The previous state of the detector is held until the next sample in flip-flop 320 and there is no drop out in the case of a continuous wet or dry condition during subsequent re-sampling.

When the diaper is dry, the flip-flop 320 produces a 0 at the Q' output. When the diaper is wet, the charge does not reach the level needed to cause the Schmidt input buffer 340 to apply a 1 to the D input of the flip-flop 320. This produces a 1 at the Q' output of the flip-flop 320 and sets off the alarm 340.

Beside the usual noise-reducing function typical of Schmidt input circuits, this Schmidt input buffer 340 provides an additional effect. As the network charging pulse voltage varies in response the power supply, so too varies the threshold voltage of the Schmidt input buffer 340. This is because the Schmidt threshold points are set by a voltage divider as a ratio directly from the supply voltage. The effect is the reduction of voltage-induced variations in the capacitance threshold as the battery voltage supply weakens.

The low pulse rate at the resistor 324 serves at least two purposes, the first of which is to produce a very long zero-voltage cycle and guarantee the complete discharge of the capacitive sensing network. Each cycle is therefore isolated from the previous one. The low duty cycle assures the bias of the external capacitive network 327, thereby eliminating the need for resistive bias components were, for instance, a comparator used and were the applied waveform a 50% duty cycle square wave. The second purpose is to limit the current required by the overall module circuit in it s repetitive testing cycle. Since the required response is in the order of one or more seconds, the period can be altered to reduce dissipation even further, though the present 10 or so microamps is adequately low.

According to an embodiment, for a duty cycle of 1:2000 for the applied pulse, the values of the resistor 324 and the threshold of the Schmidt trigger can be selected so the average power applied to the series resistor, coupling capacitors, and electrodes approximates 3 nanowatts of power.

FIGS. 4 and 5 illustrate an embodiment of a pouch. Here, an adhesive holds an outer curved flange 407 of an elastic pouch 410 against the outside of the outer water-impermeable electrically-insulating sheath 110. According to another embodiment of the invention, a thermal bond holds the flange 407 to the sheath 110. When the sensor 124 is inserted into the pouch 410, the pouch shapes itself securely about the sensor.

FIG. 6 is a plan view of the rear of an embodiment of a diaper with a pouch 410 on the outside of the sheath 110 and containing a sensor 124. FIG. 7 is an frontal elevation of the rear of the diaper, when opened, in FIG. 6. Here, the thicknesses are exaggerated for clarity. The sensor 124 in the pouch 410 carries the members 127 and presses them against the outside of the sheath 110 opposite the pads 117 printed on the inside of the sheath. A substrate 600 supports the pads 117. A layer 604 common to existing disposable diapers covers the pads 117 and the sheath 110, and provides a mounting surface for an absorber layer 607 corresponding to the layer 107. The latter is also common to most disposable diapers. Covering the absorber layer 607 is a relatively hydrophobic inner sheet 610, also common to disposable diapers, and corresponding to the sheet 104. The relatively hydrophobic fibers space the wet mass of the layer 607 from the skin of the wearer and do not conduct moisture back to the skin. This keeps the skin dry even when the wearer has wet the diaper. The urine is held away from the skin by the competition between the highly absorbent layer 607 and the not-so-absorbent sheet 610.

Figure 8:
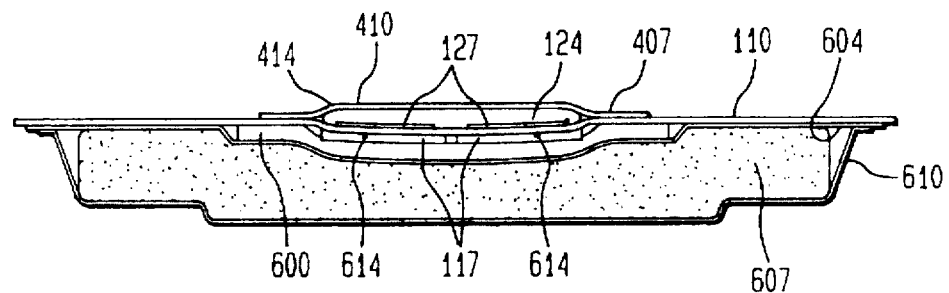
FIG. 8 is a plan view of the rear of another embodiment of a diaper with a pouch on the outside and containing a sensor.
Figure 9:
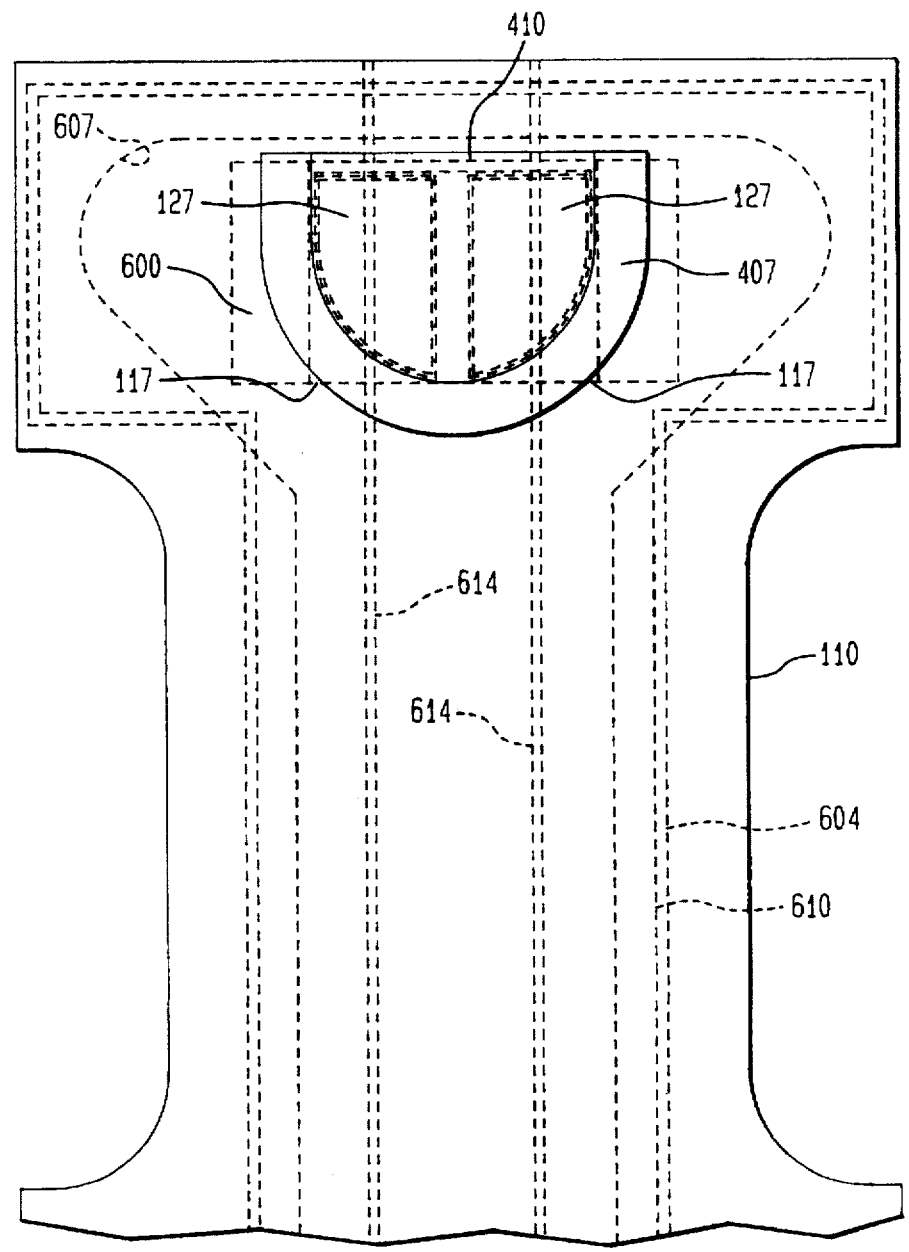
FIG. 9 is an frontal elevation of the rear of the diaper, when opened, in FIG. 8.

FIG. 8 is a plan view of the rear of another diaper similar to the diaper in FIGS. 6 and 7, but using bare wires or conductive threads 614 as the electrodes 114. FIG. 9 is an frontal elevation of the rear of the diaper, when opened, in FIG. 8. Here also, the thicknesses are exaggerated for clarity. The bare wires or conductive threads electrically connect to the pads 117 as they are squeezed between the pads and the sheath 110. According to another embodiment, the wires or conductive threads 614 pass through the absorber layer 607.

In the embodiments of FIGS. 6 to 9, as in other embodiments, when the diaper is dry the sensor 124 produces no alarm. The spaced electrodes 114 form the electrically conductive switch that remains open when the diaper is dry. Varying current from the source can then not pass through the open switch formed by the electrodes 114. When the diaper is wet, the electrolytic action of the urine in the diaper contacts the electrodes 114 and closes the switch, i.e. across the gap between the electrodes 114. The varying voltage of the source then passes a current from the sensor 124 through the capacitor formed by one member 127 and the opposing pad 117, through one electrode 114 through the electrolytically conductive gap between electrodes to the other electrrode 114, through the capacitor formed by the second of the pair of pads 117 and the second of the pair of members 127, back to the sensor. The resulting current energizes the alarm which, according to one embodiment, energizes a piezoelectric sounder and plays a tune or makes some other sound such as a beep.

According to another embodiment of the invention, the sheets 104 and 610 are omitted to give the wearer a sensation of wetness and reinforce the alarm.

According to another embodiment, the wires or threads 614 are buried in the absorber layer 607 and fixedly contact a pair of thin plates within the layer 607. The sensor 124 with the members 127 is then insulated and also buried in the absorber layer. According to another embodiment, the arrangement is the same as in FIGS. 1 to 9, but rather than using pouches, the sensor 124 with members 127 is fastened to the sheath 110 by mechanical clips, snaps, or quarter turn locking units on the outside of the diaper.

Figure 10:
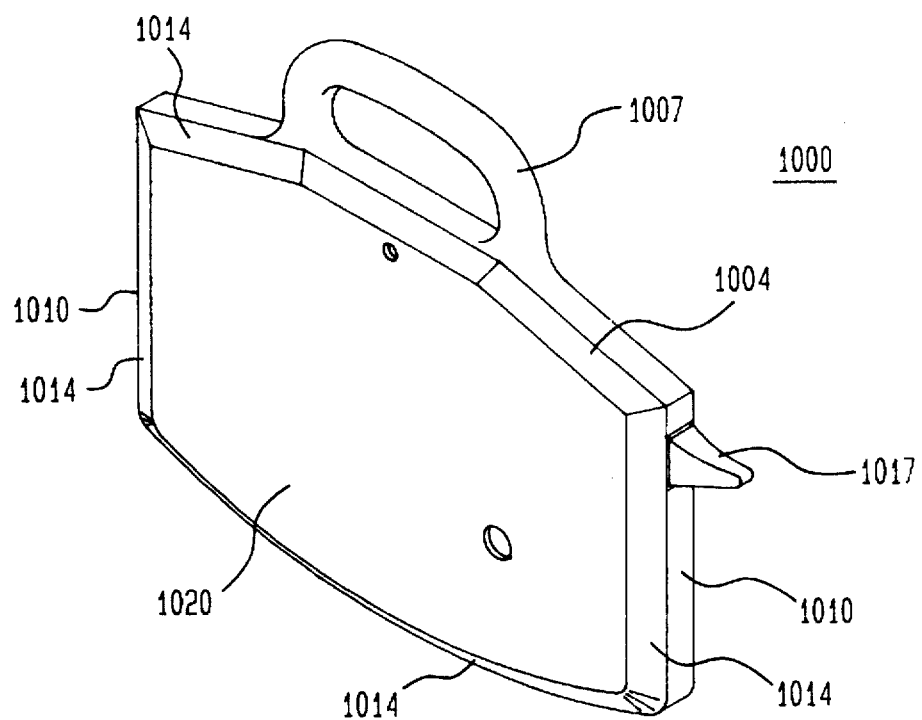
FIG. 10 is a perspective view of a sensor embodying the invention.

FIG. 10 is perspective view of an embodiment of a sensor 1000 corresponding to the sensor 124. This includes a housing 1004, an extractor tab 1007, slightly-downwardly tapered sides 1010 and beveled edges 1014. The tapered sides permit alignment on insertion into a pouch. An optional spring loaded switch 1017 is turned on when the sensor 1000 is place in a pouch. The dimensions of the sensor 1000 are such as to fit securely in a pouch. The housing has a rear face 1020 which is curved to furnish a contact force against the sheath 110 and the pouch when place in a pouch.

According to other embodiments, the pads 117 use very thin layers of metals selected for reflectivity as well as oxidation and corrosion resistance. Sputtered or vaporized aluminum covered with nickel avoids oxidation and presents an aesthetically pleasing white appearance outside the diaper.

According to other embodiments, the sensor arrangement is used to inflate a life vest when the vest touches water, in bird feeder water supplies to indicate dry conditions, security doorknobs which respond to skin moisture, liquid level sensors, plant soil moisture indicators, etc.

The invention permits a mother to tend to a newborn infant or toddler, to alert a child during toilet training that it is wetting, to help in enuresis training, and to forewarn the incontinent elderly of a problem before it arises. The invention avoids connecting the source mechanically to the conductors in the diaper from the outside. It also frees the skin of the person wearing the arrangement from direct contact with the voltages that the source applies to the electrodes. Moreover, it avoids a false alarm when the wearer sits on a wet or metal bench, leans on a wet or metal wall, or descends on a metal or wet park slide.

According to other embodiments of the invention, the non-conductive coupling from the sensor to the electrodes is optical rather than capacitive. This involves using an LED and light detector combination on opposite sides of the sheath 110. According to another embodiment, the non-conductive coupling from the sensor to the electrodes is magnetic. This involves applying an electromagnetic field from the sensor in the pouch and then having the field sensed inside the diaper. According to another embodiment, the non-conductive coupling from the sensor to the electrodes is inductive from the sensor to the electrodes.

According to another embodiment of the invention, the speed of the response of the switch formed by the electrodes 114 is varied by changing the relative hydrophobic and hydrophilic correlations of the layers 104 and 107.

The sizes of the members 127 and the pads 117 are sufficiently large, and the face to face spacing between each pad 117 and the opposing member 127 across the dielectric sheath 110 is sufficiently small, so that the capacitances 330 and 337 formed thereby are substantially greater than the very small, almost unmeasurable, stray capacitance between the side-by-side electrodes 114. The Schmidt trigger 340 is set at a low enough value, and the capacitances 330 and 337 are sufficiently high, so that even when a child sits on a wet or metal surface, the stray capacitance across the switch 334 formed by the electrodes 114 does not add enough capacitance to the series circuit 327 to drop the input to the Schmidt trigger below its positive-going threshold. Hence, the flip-flop 320 will not set off a false alarm in response to the wearer sitting on a wet or metal surface. The dimensions ar set to set off the alarm only in response to conduction across the switch 334 formed by the electrodes 114.

While embodiments of the invention have been described in detail it will be evident to those skilled in the art that the invention may be embodied otherwise without departing from its spirit and scope.

What is claimed is:

1. A wetness detector for a detecting electrolytic wetness in a first area, said first area being subject to wetness, comprising:
    a first electrode projecting into the first area;
    a second electrode spaced from the first electrode and projecting into the first area;
    a sensing device in a second area protected from wetness in said first area and non-conductively coupled to each of said electrodes and responsive to the impedance between said electrodes in said first area so as to produce a signal when the first area becomes wet and electrolytic wetness couples the electrodes in the first area.

2. A wetness detector as in claim 1, wherein said sensing device is capacitively coupled to said first and second electrodes.

3. A wetness detector as in claim 1, wherein said sensing device includes a first conductor in said second area protected from the wetness of said first area and capacitively coupled to said first electrode and a second conductor in said second area protected from wetness of said first area and capacitively coupled to said second electrode.

4. A wetness detector as in claim 1, wherein said sensing device includes a source of varying voltage coupled non-conductively to said first and second electrodes and a signal output responsive to reduction of impedance between said electrodes.

5. A wetness detector as in claim 2, wherein said sensing device includes a source of varying voltage coupled capacitively to said first and second electrodes and a signal output.

6. A wetness detector as in claim 3, wherein said sensing device includes source of varying voltage connected to said first conductor and to said second conductor, and further includes a signal output responsive to reduction of resistance between said electrodes.

7. A wetness detector as in claim 1, wherein said sensing device includes a signal output responsive to reduction of resistance between said electrodes.

8. A wetness detector as in claim 7, wherein said signal output is audible.

9. A wetness detector as in claim 7, wherein said signal output is visible.

10. A wetness detector as in claim 7, wherein said signal output is in the form of radio waves.

11. A wetness detector as in claim 7, wherein said signal output is in the form of infra-red radiation.

12. A wetness detector as in claim 7, wherein said coupling is capacitive, said sensing device having a pair of fixedly spaced planar conductors and said electrodes having a pair of fixedly spaced pad shaped conductors respectively capacitively coupled to said planar conductors, one of said pair of conductors being larger than the other of said conductors to permit misalignment of said conductors relative to each other without changing capacitance between said conductors.

13. A wetness detector for a detecting electrolytic wetness as in claim 1, wherein said first area includes a section subject to wetness and a second section which remains substantially dry, and wherein said first and second electrodes extend from the first section to the second section and said sensing device in the second area protected from wetness is non-conductively coupled to each of said electrodes at the second section.

14. A wetness detector for a detecting electrolytic wetness, as in claim 13, wherein said first area is the inside of a non-conductive liquid-resistant part of a diaper and the second area is outside the non-conductive liquid-resistant part of a diaper, and the first section is near the crotch of the diaper and the second section is near the waist of the diaper, said sensing device being in the second area near the waist.

15. A diaper, comprising:
    an absorbent portion;
    a liquid resistant portion having first and second faces and lining the absorbent portion along the first face;
    a pouch on the second face of the liquid resistant portion;
    a first electrode extending along said absorbent portion and projecting along the first face of the liquid resistant portion opposite the pouch;

a second electrode spaced from the first electrode and extending along said absorbent portion and projecting along the first face of the liquid resistant portion opposite the pouch;

said first and second electrodes projecting along the absorbent portion opposite the pouch and being insulated from said pouch so as to non-conductively couple to contents in the pouch.

16. A diaper as in claim 15, wherein said electrodes have enlarged portions opposite said pouch.

17. A diaper as in claim 15, wherein said electrodes are coated on plastic material.

18. A diaper as in claim 15, wherein said electrodes are conductive areas on a water permeable substrate.

19. A diaper as in claim 15, wherein said electrodes are conductive wires.

20. A diaper as in claim 15, wherein said electrodes are conductive threads woven into the absorbent material.

21. A diaper as in claim 15, wherein said electrodes are printed on said liquid resistant portion.

22. A diaper as in claim 15, wherein said pouch contains a sensor non-conductively coupled to said electrodes.

23. A diaper as in claim 15, wherein said pouch contains a sensor capacitively coupled to said electrodes.

24. A diaper as in claim 22, wherein said sensor includes a source of varying voltage and an alarm responsive to urine induced lowered resistance between said electrodes.

25. A diaper as in claim 22, wherein said sensor includes a pair of conductive plate-shaped members opposing said electrodes across said liquid resistant portion.

26. A diaper in claim 22, wherein said coupling is capacitive, said sensor having a pair of fixedly spaced planar conductors and said electrodes having a pair of fixedly spaced pad shaped conductors respectively capacitively coupled to said planar conductors, one of said pair of conductors being larger than the other of said conductors to permit misalignment of said conductors relative to each other without changing capacitance between said conductors.

27. A diaper as in claim 15, wherein said diaper has a crotch section and a waist section, said pouch being substantially in the vicinity of the waist section and said first and second electrodes extending substantially from the waist section to the crotch section.

28. A wetness detector for placement in a pouch on an outside of a non-conductive waterproof sheath of a diaper having an absorber inside the sheath and a pair of electrodes extending into the absorber and along a inside of the sheath opposite the pouch, comprising:

a source of varying voltage;

a pair of conductive members coupled to said source of varying voltage and spaced from each other for placement against the outside of the non-conductive sheath within the pouch so as to create a non-conductive coupling between said members outside of the non-conductive sheath and the electrodes inside the non-conductive sheath; and an alarm coupled to said conductive members and responsive to detection of low impedance between the electrodes.

29. A detector as in claim 28, wherein said alarm is audible.

30. A detector as in claim 28, wherein said alarm is electromagnetic.

31. A detector as in claim 28, wherein said alarm is visible.

32. A detector as in claim 28, wherein said alarm is in the form of radio waves.

33. A detector as in claim 28, wherein said alarm is in the form of infrared radiation.

34. A detector as in claim 28, wherein said members are plate shaped for capacitive coupling with electrodes in the diaper.

35. A detector as in claim 28, further including a housing, said housing having tapered and beveled edges.

36. A detector as in claim 35, wherein said housing includes an extractor tab.

37. A detector as in claim 35, wherein said housing includes a spring loaded switch.

38. A detector as in claim 35, wherein said housing has a curved surface.

39. A detector as in claim 28, wherein said alarm produces tactilely-sensible vibrations.

40. A detector as in claim 35, wherein said alarm is audible.

41. A detector as in claim 35, wherein said alarm is visible.

42. A detector as in claim 35, wherein said alarm is electromagnetically detectable.

43. A detector as in claim 28, wherein said diaper has a crotch section and a waist section, said pouch being substantially in the vicinity of the waist section and said electrodes extending substantially from the waist section to the crotch portion.

* * * * *